United States Patent [19]

Share

[11] Patent Number: 5,756,742
[45] Date of Patent: May 26, 1998

[54] POLYMERIZABLE COMPOUNDS

[75] Inventor: Paul E. Share, Moon Township, Pa.

[73] Assignee: Henkel Corporation, Plymouth Meeting, Pa.

[21] Appl. No.: 577,569

[22] Filed: Dec. 22, 1995

[51] Int. Cl.$^6$ .................. C07D 295/18; C07D 295/192
[52] U.S. Cl. ............................ 544/357; 544/387
[58] Field of Search ....................... 544/357, 387

[56] References Cited

U.S. PATENT DOCUMENTS

| Re. 29,131 | 2/1977 | Smith et al. | 260/77.5 |
|---|---|---|---|
| 3,352,866 | 11/1967 | Dornfeld | 544/386 |
| 3,510,247 | 5/1970 | Tesoro et al. | 8/116.2 |
| 3,528,964 | 9/1970 | Tesoro | 260/231 |
| 3,935,330 | 1/1976 | Smith et al. | 427/41 |
| 4,215,195 | 7/1980 | Ponticello et al. | 430/496 |
| 4,220,646 | 9/1980 | Cortrel et al. | 544/373 |
| 4,247,673 | 1/1981 | Ponticello et al. | 526/263 |
| 4,346,231 | 8/1982 | Ponticello et al. | 560/178 |
| 4,940,793 | 7/1990 | Botre et al. | 544/386 |
| 5,045,427 | 9/1991 | Hara | 430/138 |
| 5,138,027 | 8/1992 | Van Beek | 528/339 |
| 5,192,766 | 3/1993 | Nakamura et al. | 514/255 |
| 5,563,214 | 10/1996 | Share et al. | 524/809 |
| 5,565,567 | 10/1996 | Share | 524/809 |

FOREIGN PATENT DOCUMENTS

| 053047 | 6/1982 | European Pat. Off. |
| 0356960 | 3/1990 | European Pat. Off. |
| 9429296 | 12/1994 | WIPO |

OTHER PUBLICATIONS

M. Taningher et al., "Genotoxicity of N-acryloyo-N'-phenylpiperazine, a Redox Activator for Acrylic Resin Polymerization," *Mutation Reseach*, vol. 282, pp. 99–105 (1992).
*Encyclopedia of Polymer Science and Engineering*, vol. 3, pp. 552–675; John Wiley & Sons, New York. (1985).
Thomas et al., Acrylate Polymers, *Encyclopedia of Polymer Science and Engineering*, vol. 1, 169–211; John Wiley & Sons, New York. (1985).
*Encyclopedia of Polymer Science and Engineering*, supp. vol. pp. 53, 109, 110, John Wiley & Sons, New York. (1985).
*Encyclopedia of Chemical Technology*, vol. 2, pp. 252–258; vol. 2, pp. 67, 68 and pp. 795, 803–806; vol. 12, pp. 319–321; vol. 9, pp. 306–308; John Wiley & Sons, New York. (1978).
E. J. Murphy et al., "Some Characteristics of Steric Polymerization", *Proceedings of Rad Tech—North America*, vol. 1, pp. 217–226. (1990).
Body et al., "1,2-Epoxide Polymers", *Encyclopedia of Polymer Science and Engineering*, vol. 6, pp. 223–322 (John Wiley & Sons, New York, New York 1986).
*Encyclopedia of P. Science & Engineering*, vol. 11, pp. 476–489 (John Wiley & Sons, Inc., NY, NY 1988).

R. Larock, *Comprehensive Organic Transformations: A Guide to Functional Group Preparations*, pp. 978 and 979 (VCH Publishers, NY, NY 1989).
Chemical and Pharmaceutical Bulletin, (issued 1984), Shiozawa et al., "Antivertigo Agents. IV. Synthesis and Antivertigo Activity of 6-[w-(4-Aryl-1-piperazinyl)alkyl]-5,6,7,8,-tetrahydro-1,6-naphthyridines", pp. 3981–3993.
Przybilla et al, Chemical Abstracts, vol. 118, No. 222894 (1993).

*Primary Examiner*—Emily Bernhardt
*Attorney, Agent, or Firm*—Wayne C. Jaeschke; John Daniel Wood; Daniel S. Ortiz

[57] ABSTRACT

Polymerizable compounds based on N-acylamido-piperazines are provided. Such compounds have the formula:

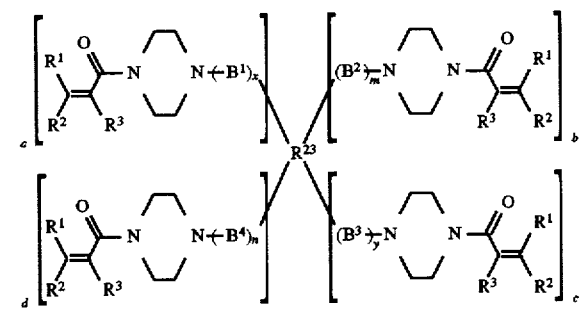

wherein:

a, b, c and d are independently 0 or 1 and the sum of a, b, c and d is at least 3.
$R^1$, $R^2$, and $R^3$ are hydrogen and/or lower alkyl.
$B^1$, $B^2$, $B^3$, and $B^4$ are independently carbonyl, sulfonyl, amide, or carboxyl;
m, n, x, and y are independently one or zero;
$R^{23}$ is a group selected from, substituted and unsubstituted phenyl and phenonyl.

These compounds are particularly useful as polymerizable monomers in radiation curable coatings. The compound preferably has at least one group

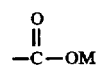

substituted on $R^{23}$ wherein M is H or a counterion to the carboxyl group which can be present in place of a

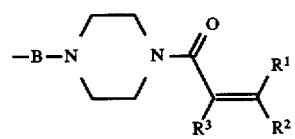

group.

17 Claims, No Drawings

POLYMERIZABLE COMPOUNDS

FIELD OF THE INVENTION

The present invention relates to polymerizable compounds and to their use. More particularly, it relates to N,N'-substituted piperazine acrylamide compounds and to processes of polymerizing these compounds, e.g. for preparing coatings.

BACKGROUND OF THE INVENTION

The use of N,N'-substituted piperazine is disclosed in a number of documents. U.S. Pat. No. 5,192,766 purports to disclose N-acryloylpiperazine derivatives and their pharmaceutical use as platelet activating factor antagonists. While the title uses the term N-acryloylpiperazine, it is clear from the disclosure that the compounds disclosed have a phenyl substituent bonded to the alpha,beta-unsaturated acylamido group such that the compounds are, thus, apparently cinnamoyl derivatives or homologues thereof.

M. Taningher et al., "Genotoxicity of N-acryloyl-N'-phenylpiperazine, a Redox Activator for Acrylic Resin Polymerization", *Mutation Research*, vol. 282, pp. 99–105 (1992) discusses the use of N-acryloyl-N'-phenylpiperazine as a promoter of redox reactions in place of other tertiary aromatic amines, e.g. N,N-dimethylaniline. It is speculated that the acryloyl group will allow the compound to be copolymerized into the final material and thus avoid release thereof into the environment.

U.S. Pat. No. 5,045,427 discloses the use of a variety of polymerizable compounds, including N,N'-bis-acrylamido-piperazine, in a photographic material. This photographic material is comprised of a support on which is provided a light-sensitive layer comprised of a photosensitive silver halide, a non-photo-sensitive silver salt, a reducing agent, a color image-forming material and a polymerizable compound.

EP-0356960 discloses polyacrylamide gels which employ as crosslinking agents diacylyl compounds with tertiary amide groups, e.g. diacrylyl piperazine (a.k.a. N,N'-bis-acrylamido-piperazine). These gels contain a chaotropic agent which permits the use of the gels in the separation of proteins or nucleic acids.

U.S. Pat. No. 3,510,247 discloses the modification of cellulosic materials with tertiary bis-acrylamides, e.g. diacryloyl piperazine (a.k.a. N,N'-bis-acrylamido-piperazine). The bis-acrylamide is applied to the cellulosic substrate and a crosslinking reaction is catalyzed by the use of an alkaline compound and elevated temperatures, generally 200 degrees F to 350 degrees F. U.S. Pat. No. 3,528,964 discloses a similar modification, but the amides are sulfonic acid amides, wherein the sulfonic acid groups contain ethylenic unsaturation.

The technology for the production of coatings by curing monomeric compositions on the surface of various substrates is generally known. For example, J. Lowell, "Coatings", *Encyclopedia of Polymer Science and Engineering*, vol. 3, pp. 615–675, discusses, at page 647, the production of coatings by free-radical polymerization of monomers, e.g. unsaturated polyesters in a solution of an unsaturated monomer such as styrene, acrylates, and methacrylates, and polyfunctional low volatility monomers such as trimethylolpropane triacrylate. When such systems are cured with ultra-violet radiation, a photoinitiator such as benzophenone is often used to increase the production of free-radicals and thereby promote curing of the coating.

While N,N'-bis-acrylamido-piperazine is a useful monomer in many applications, it has been found its performance as the major component of a radiation curable composition has certain drawbacks. For example, it has been observed that cured films thereof are quite brittle.

SUMMARY OF THE INVENTION

This invention relates to compounds of the formula I:

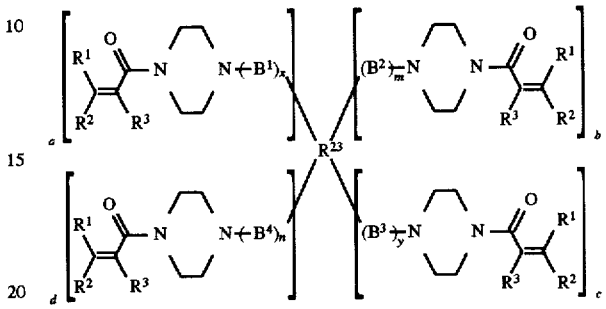

wherein:

$R^1$, $R^2$, and $R^3$ are each independently selected from the group consisting of hydrogen and lower alkyl (preferably $R^1$ and $R^2$ are hydrogen and $R^3$ is hydrogen or methyl), $B^1$, $B^2$, $B^3$, and $B^4$ are linking groups independently selected from the group consisting of carbonyl, sulfonyl, amide, and carboxyl;

a, b, c, and d are independently one or zero, provided that the sum of a, b, c, and d is at least two;

m, n, x, and y are independently one or zero;

$R^{23}$ is a radical selected from the group consisting of phenyl, substituted phenyl, phenonyl (preferably benzophenonyl), and substituted phenonyl (preferably substituted benzophenonyl). In certain embodiments, $R^{23}$ is a substituted phenyl, the number of substituents not exceeding the difference of six and sum of m, n, x, and y. By "phenonyl" group is meant a radical having a phenyl group wherein one of the ring hydrogen atoms of the phenyl group has been replaced by the carbon atom of a ketone carbonyl group. Likewise, by "benzophenonyl" is meant a phenonyl radical wherein the ketone is a diphenyl ketone.

A preferred class of compounds within the scope of this invention have the formula II:

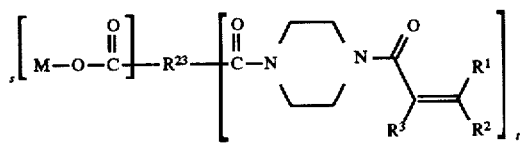

wherein each $R^1$, $R^2$, and $R^3$ is independently selected from the group consisting of hydrogen and lower alkyl, $R^{23}$ is a radical selected from the group consisting of phenyl, substituted phenyl, phenonyl (preferably benzophenonyl), and substituted phenonyl (preferably substituted benzophenonyl);

s and t are integers, preferably each of s and t is 2; and

M is hydrogen or a counter-ion of a salt of said compound. It has been found that when a compound of formula II is used in a polymerizable composition, the cured composition exhibits excellent adhesion to the substrate on which it is cured.

This invention also relates to a polymerizable composition comprising a compound of formula I, above, and to a method of coating a substrate comprising (i) contacting a surface of a substrate with a polymerizable composition comprising a compound of formula I, above, and (ii) exposing said surface to radiation sufficient to cause said compound to polymerize in contact with said surface. In preferred methods, said compound is present in said composition in a major amount (i.e. at least 50%) on a mole percent basis of all of the monomers of said polymerizable composition.

This invention also relates to a process of making a compound having the structural formula II:

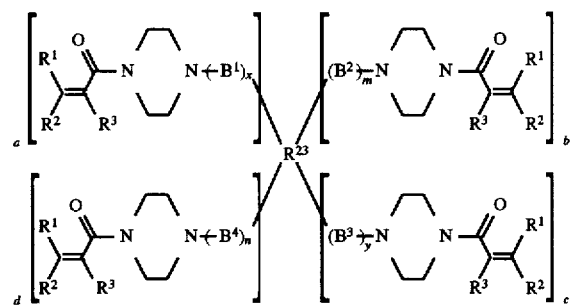

wherein:

$R^1$, $R^2$, and $R^3$ are each independently selected from the group consisting of hydrogen and lower alkyl (preferably $R^1$ and $R^2$ are hydrogen and $R^3$ is hydrogen or methyl), $B^1$, $B^2$, $B^3$, and $B^4$ are linking groups independently selected from the group consisting of carbonyl, sulfonyl, amide, and carboxyl;

a, b, c and d are independently one or zero, provided that the sum of a, b, c, and d is at least two;

m, n, x, and y are independently one or zero;

$R^{23}$ is a radical selected from the group consisting of phenyl, substituted phenyl, phenonyl (preferably benzophenonyl), and substituted phenonyl (preferably substituted benzophenonyl), by reacting a compound having the formula A:

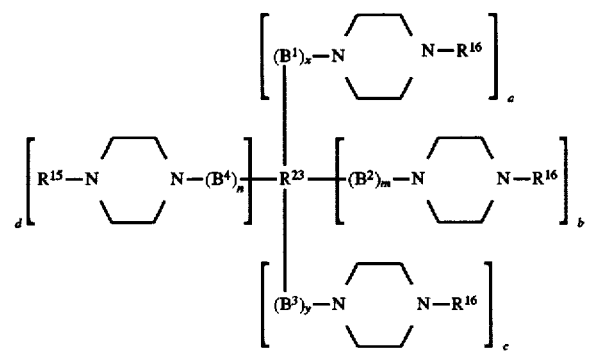

wherein $R^{15}$ and $R^{16}$ are hydrogen or an organic group susceptible to displacement, with a compound having the formula B:

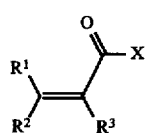

wherein $R^1$, $R^2$, and $R^3$ are as defined above and X is a leaving group, said reactants being in the presence of a catalyst for said reaction.

DETAILED DESCRIPTION OF THE INVENTION

This invention relates to novel compounds of this invention, e.g. compounds of formula I, and to methods which employ these novel compounds. These compounds are piperazine derivatives in which one of the amine nitrogen atoms of the piperazine molecule has been reacted with an acylating agent to introduce the acrylamido group (or a homologue thereof) which contains the groups $R^1$, $R^2$, and $R^3$, and in which the other piperazine nitrogen atom has been reacted with a compound to introduce the $R^{23}$ group (and optionally a B linking group) into the molecule. Thus, one of the starting materials for preparing the novel compounds of this invention is piperazine, or a derivative thereof (e.g. an amide that is susceptible to trans-amidation).

Because piperazine has secondary amine groups, there is a possibility that compositions prepared therefrom will contain residual free secondary amine, e.g. from unreacted piperazine or a piperazinyl-functional intermediate. It is believed that the presence of even small amounts of such impurities can lead to gelation of compositions which contain compounds of formula I. Such gelation is believed to be caused by reaction of the residual free secondary amine with the ethylenic unsaturation of the compounds of formula I.

The composition of the invention should not gel when held at a temperature of 60° C. for an extended period of time, preferably at least about 150 hours, more preferably at least about 175 hours, and even more preferably at least about 200 hours. The compositions of this invention will typically not gel after at least 300 hours at 60° C. and most preferably at least about 450 hours.

A means of evaluating the stability of the compositions of this invention with respect to gelation is to subject the composition to heat aging and to measure the viscosity of the aged composition. For example, the viscosity of the composition is measured, e.g. at an ambient temperature of 25° C. Then, the composition is aged by placing it in an oven at 60° C. After aging and cooling to an ambient temperature of 25° C., the viscosity of the composition is then measured again. If there is a significant increase in the viscosity of the composition after such aging, the composition thus shows a tendency to gel. Preferably, the composition will show an increase in viscosity of less than 100%, more preferably less than 50%, and even more preferably less than 20%, after a period at 60° C. of at least about 3 hours, more preferably, at least about 24 hours and even more preferably at least about 150 hours. Ideally, the composition will show no increase in viscosity that is measurable within the limits of detection of the apparatus and procedure chosen after being held for more than 150 hours at 60° C. An example of a useful viscometer is a cone and plate viscometer available as the Carri-Med CSL Rheometer, distributed by Mitech Corp., Twinsburg, Ohio, and manufactured by Carri-Med Ltd., Dorking, Surrey, UK.

Because it the presence of free secondary amine groups which is thought to cause gelation of compositions containing compounds of this invention, it is believed that methods of making the compositions of this invention which minimize the presence of residual free secondary amine will be useful in preparing compositions of this invention. Such methods include the use of a catalyst, as discussed more fully below, for the reactions which consume the free secondary amine functionality of the piperazine starting material and/or piperazinyl intermediate.

Also, techniques to reduce the reactivity of the mixture, such as the inclusion of polymerization inhibitors in the composition. A preferred polymerization inhibitor in this regard is phenothiazine. Quinones, e.g. methyl hydroquinone is also useful as an inhibitor, but the mechanism of inhibition of quinones such as methyl hydroquinone requires the presence of oxygen for effective inhibition and it may not be practical to maintain sufficient levels of oxygen in the compositions to allow the use of such inhibitors.

The group $R^{23}$ is a phenyl group, a substituted phenyl group, a phenonyl group or a substituted phenonyl group. The substituted phenyl and phenonyl groups are phenyl or phenonyl groups wherein one or more hydrogen atoms are replaced by an atom or a group of atoms other than hydrogen including the alkyl, alkenyl, alkoxy, halogens, nitrogen, sulfur, oxygen, and phosphorus or groups of heteroatoms such as nitro, sulfonic acid, $C_{1-10}$ alkyl sulfonate ester, sulfoxide, sulfone, phosphoryl, trihalomethyl, and the like.

The B linking group, if present, is introduced into the molecule by the derivatization of one of the piperazine nitrogen atoms. The B linking group is a carbonyl, sulfonyl, amide, or carboxyl group, i.e. a group having the respective formula:

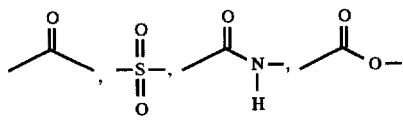

In each respective case, the compound will then have at that piperazine nitrogen atom an amide functionality, a sulfonamide functionality, a substituted-urea functionality, or a urethane functionality. Because the piperazine nitrogen atom can be covalently bonded to the $R^{20}$ group directly, a B linking group may not be present and, thus, n may be zero (in which case there will be a tertiary amine functionality at that piperazine nitrogen atom).

Compounds of formula I can be prepared by the following general reaction scheme:

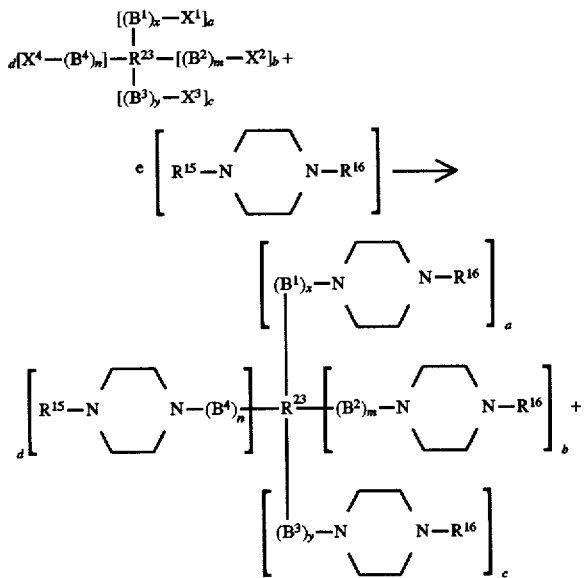

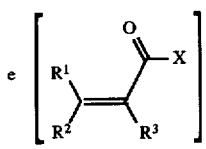

wherein the variables are as set forth above, each of $X^1$, $X^2$, $X^3$, and $X^4$ is a leaving group and "e" is equal to the sum of a, b, c, and d.

The choice of the reactant $_a[X^1\text{-}(B^1)_x]\text{-}R^{23}\text{-}[(B^2)_m\text{-}X^2]_b($ $[(B^3)_y\text{-}X^3]_c)([(B^4)_n\text{-}X^4]_d)$ will determine the nature of the $B^1$, $B^2$, $B^3$, and $B^4$ linking groups that are introduced into the molecule. When there is no such linking group, the reactant will typically be an alkyl halide or an aryl alkaline earth metal halide (e.g. the Grignard reagent phenyl magnesium bromide). Alkylation of amines is discussed in *Encyclopedia of Chemical Technology*, vol. 2, pp. 67 and 68 (Kirk-Othmer, eds., John Wiley & Sons, Inc., N.Y., N.Y., 1978), the disclosure of which is incorporated by reference.

When the B linking group is a carbonyl group, the reactant will typically be an acid halide or anhydride and the product can be characterized as an acylamide. Acylation reactions are discussed in *Encyclopedia of Chemical Technology*, vol. 2, pp. 252–258 (Kirk-Othmer, eds., John Wiley & Sons, Inc., N.Y., N.Y., 1978), the disclosure of which is incorporated by reference. In the preferred method of preparing the preferred compounds of this invention, the reactant is a tetra-carboxylic acid dianhydride of benzene or benzophenone. In this reaction, two moles of piperazine are reacted with one mole of the anhydride reactant. Because the anhydride group is much more reactive with the piperazine than the carboxylic acid group that is formed upon reaction of the anhydride, the product of the reaction of two moles of piperazine reacted with one mole of the anhydride reactant will result in an intermediate product that consists essentially of a compound of having two free carboxylic acid groups and two piperazine amide groups and will contain essentially none of the compound having one free carboxylic acid group and three piperazine amide groups.

When the B linking group is a sulfonyl group, the reactant will typically be a sulfonyl halide and the product can be characterized as a sulfonamide. The reaction to form a sulfonamide is very similar to an acylation reaction. The synthesis of sulfonamides is discussed in *Encyclopedia of Chemical Technology*, vol. 2, pp. 795 and 803–806 (Kirk-Othmer, eds., John Wiley & Sons, Inc., N.Y., N.Y., 1978), the disclosure of which is incorporated by reference.

As discussed above, when the B linking group is an amide, the reactant will typically be an isocyanate. The synthesis of urea compounds by the reaction of an amine with an isocyanate is discussed in *Encyclopedia of Chemical Technology*, vol. 12, pp. 319–321 (Kirk-Othmer, eds., John Wiley & Sons, Inc., N.Y., N.Y., 1980), the disclosure of which is incorporated by reference.

The reaction to introduce the acrylamide functionality into the molecule is an acylation reaction. Acylation techniques for amide formation are generally described in *Encyclopedia of Chemical Technology*, vol. 2, pp. 252–258 (Kirk-Othmer, eds., John Wiley & Sons, Inc., N.Y., N.Y., 1978), the disclosure of which is incorporated by reference. In the acylation of an amine, an acylating compound of the desired molecular formula with a leaving group is reacted with the amine compound. For example, an carboxylic acid, acid anhydride or acid halide (e.g., chloride, of acrylic or methacrylic acid) is reacted with the amine, or derivative thereof, optionally in the presence of a catalyst, e.g. a tertiary amino-functional pyridine, for example, N,N-dimethylaminopyridine. When the carboxylic acid form of the acylating agent (i.e. leaving group is a hydroxyl group) is used, a strong acid catalyst, e.g. p-toluenesulfonic acid, is typically employed.

The reaction is typically accomplished in an inert solvent, but the catalyst or one of the reactants may also act as a solvent. Because piperazine is hydrophilic, but the reaction product tends to be less so, the choice of solvent and reaction conditions can affect the efficiency of the reaction. Generally, it has been found that an organic solvent having a greater polarity than an aromatic solvent (e.g. toluene) is preferred, for example, a mixture of acetonitrile and dichloromethane (e.g. 1:1 by volume) is a preferred solvent.

Because piperazine is a secondary amine, an acylating agent with a more labile leaving group (e.g. an acid halide wherein the leaving group is a halogen anion such as chloride) is preferred. With such a leaving group, a hydrohalic acid (e.g. hydrochloric acid) is a by-product of the reaction, and thus, an alkaline material should be added to the reaction mixture to neutralize by-product acid. It has been found that inorganic alkaline materials, e.g. alkali metal carbonates, are less preferred due to problems associated with product isolation and that lower alkyl tertiary amine bases (having the formula $NR^1R^2R^3$ wherein $R^1$, $R^2$, and $R^3$ are independently $C_1$ to $C_4$ alkyl, e.g. triethylamine) are useful in neutralizing acid formed during an acylation reaction which employs an acyl halide as the acylating agent.

The polymerizable components useful in this invention are any materials which are capable of addition copolymerization with the N,N'-acrylamido-piperazine compounds of formula I described above to form a useful polymer composition. The polymerization of acrylamide monomers is discussed in *Encyclopedia of Polymer Science and Engineering*, vol. 1, pp. 169–211 (John Wiley & Sons, Inc., N.Y., N.Y., 1985), the disclosure of which is incorporated by reference. The polymerizable components include monoethylenically unsaturated monomers capable of homopolymerization, or copolymerization with other ethylenically unsaturated monomers, as well as copolymerization with the compound. Examples of suitable monoethylenically unsaturated compounds include alkyl acrylates, alkyl methacrylates, vinyl esters, vinyl amines and vinyl aromatic compounds. Specific examples include ethyl acrylate, t-butyl acrylate, 2-ethylhexyl acrylate, methyl methacrylate, lauryl methacrylate, vinyl acetate, N-vinyl pyrrolidinone, styrene, and vinyl toluene.

Polymerizable compounds which may be used in the present invention are addition-polymerizable monomers and oligomers and polymers thereof. Addition-polymerizable monomers are compounds having one or more carbon-carbon unsaturated bonds. Examples of the compounds are acrylic acid and salts thereof, acrylates (e.g. lower alkyl acrylates), acrylamides (e.g. lower N-alkyl acrylamides), methacrylic acid and salts thereof, methacrylates, methacrylamides, maleic anhydride, maleates, itaconates, styrenes, vinyl ethers, vinyl esters, N-vinyl-heterocyclic compounds, allyl ethers, and allyl esters and derivatives thereof.

In addition, a crosslinking compound having an activity of increasing the degree of hardening or the viscosity of the formed polymeric compounds, by crosslinking the polymeric the coating can be employed. Such crosslinking compounds are so-called poly-functional monomers having a plurality of ethylenic or vinyl groups or vinylidene groups in the molecule. This addition will be especially useful if the N,N'-substituted acylamido-piperazine compound chosen has only one ethylenic unsaturation, e.g. N-(o-alkylphthalamido),N'-acrylamido-piperazine.

Examples of a number of the various polymerizable compounds which may be included in the polymerizable compositions of the present invention include acrylic acid, methacrylic acid, butyl acrylate, methoxyethyl acrylate, butyl methacrylate, acrylamide, N,N-dimethylacrylamide, N,N-diethylacrylamide, N-acrylamido-morpholine, N-acrylamido-piperidine, glycidyl acrylate, 2-ethylhexyl acrylate, acrylic acid anilide, methacrylic acid anilide, styrene, vinyltoluene, chlorostyrene, methoxystyrene, chloromethylstyrene, 1-vinyl-2-methylimidazole, 1-vinyl-2-undecylimidazole, 1-vinyl-2-undecylimidazoline, N-vinylpyrrolidone, N-vinylcarbazole, vinylbenzyl ether, vinylphenyl ether, methylene-bis-acrylamide, trimethylene-bis-acrylamide, hexamethylene-bis-acrylamide, N,N'-diacrylamidopiperazine, m-phenylene-bis-acrylamide, p-phenylene-bis-acrylamide, ethylene glycol diacrylate, propylene glycol dimethacrylate, diethylene glycol diacrylate, polyethylene glycol diacrylate, bis(4-acryloxypolyethoxyphenyl)propane, 1,5-pentanediol diacrylate, neopentyl glycol diacrylate, 1,6-hexanediol acrylate, polypropylene glycol diacrylate, pentaerythritol triacrylate, trimethylolpropane triacrylate, pentaerythritol tetraacrylate, N-methylol-acrylamide, diacetone-acrylamide, triethylene glycol dimethacrylate, pentaerythritol tetra-allyl ether.

Examples of useful reactive oligomers include low molecular weight polymers (e.g., about 1,000 to 25,000 g/mole) having polymerizable ethylenic unsaturation. Specific examples include maleic-fumaric unsaturated polyesters, acrylate-terminated polyesters (e.g. those described in U.S. Pat. No. Re 29,131 to Smith et al.) acrylic copolymers having pendant vinyl unsaturation (e.g. allyl acrylate/acrylic copolymers), epoxy acrylates, and polyurethane acrylates.

Examples of useful reactive polymers include graft polymerizable polyolefins, e.g., polyethylene, polypropylene, and ethylene/propylene copolymers, and polymers having polymerizable ethylenic unsaturation along the backbone, for example diene homopolymers or copolymers (e.g., styrene-butadiene copolymers, cis-polybutadiene, and butadiene-acrylonitrile copolymers).

The polymerizable component and N,N'-acylamido-piperazine compound can be mixed in any convenient manner which will place the component and compound in a sufficiently reactive association to form a polymer on subsequent curing thereof. Generally, simple mixing of the polymerizable component and N,N'-acylamido-piperazine compound will suffice. Other useful techniques include conventional wet chemistry techniques, e.g., dissolution in a common solvent system.

The amount of the N,N'-acylamido-piperazine compound in the polymerizable composition will vary depending upon the contemplated application of the cured polymeric composition, but will generally be sufficient to detectably affect the properties of the polymer and/or crosslink the polymeric composition. The affect on the properties of the polymer and/or degree of crosslinking of the cured polymeric composition can be determined by conventional techniques, e.g., adhesion to substrates, resistance to solvents (e.g., swelling, extractibles, and/or spot-testing). In preferred compositions, the amount of a diacrylamidopiperazine compound will be sufficient to measurably increase the gel content of the cured polymeric composition, e.g., preferably by at least about 1% and more preferably at least about 5%. Typical levels of N,N'-acylamido-piperazine compound that have only one ethylenic unsaturation will range from about 5 mole % to about 90 mole %, preferably from about 10 mole % to about 50 mole %, of the polymerizable components of the polymerizable composition.

The polymerizable composition of the present invention can be applied to a variety of substrates. These include, for example, porous stock such as paper and cardboard, wood and wood products, metals such as aluminum, copper, steel, and plastics such as P.V.C., polycarbonates, acrylic and the like. After addition of a suitable photoinitiator, e.g., PHOTOMER 51® brand photoinitiator (benzyl dimethyl ketal), the compositions are applied by methods such as spraying, rollcoating, flexo and gravure processes onto a selected substrate. The resulting coated substrate, e.g., a paper, is typically cured under a UV or electron beam radiation. The compositions may optionally include other substances such as pigments, resins, monomers and additives such as anti-oxidants and rheological modifiers. For example, flow and levelling agents, e.g. BYK-307 and/or BYK 310, available form BYK-Chemie USA, Wallingford, Conn., can be used to modify the coating characteristics of the polymerizable composition. Methods of coating and materials used in coatings are described in *Encyclopedia of Polymer Science and Engineering*, vol. 3, pp. 552–671 and supp. vol., pp. 53, 109 and 110 (John Wiley & Sons, Inc., N.Y., N.Y., 1985), the disclosure of which is incorporated by reference.

The coated surface is then exposed to sufficient energy, e.g. heat or electromagnetic radiation to cure the composition through the reactive pi bonds. Suitable sources of radiation include ultraviolet light, electron beam or radioactive sources such as are described in U.S. Pat. No. 3,935,330 issued Jan. 27, 1976 to Smith et al. To enhance the rate of curing free radical initiators may be included in the composition such as benzoin, benzoin ethers, Michler's Ketone and chlorinated polyaromatic hydrocarbons. Other free radical initiators are ordinarily organic peroxides, hydroperoxides, peroxy acids, peroxy esters, azo compounds, ditertiary butyl peroxide, benzoyl peroxide, 2,4-dichlorobenzoyl peroxide, tertiary butyl hydroperoxide, 1,5-dimethyl-2,5-bis (hydroperoxy)-hexane, peroxyacetic acid, peroxybenzoic acid, tertiary butyl peroxypivalate, tertiary butyl peroxyacetic acid and azobisisobutyronitrile. The free radical initiator is typically present at from about 0.01 to about 20% by weight of the radiation curable components. To ensure that the composition does not prematurely polymerize, a free radical inhibitor may be added to the polymerizable composition. Examples of suitable inhibitors include hydroquinone and the methyl ether thereof or butylated hydroxy toluene at a level of from about 5 ppm to about 2000 ppm by weight of the polymerizable components.

Particularly preferred sources of radiation emit electromagnetic radiation predominantly in the ultra-violet band. When such a source is used, the polymerizable composition preferably contains a photoinitiator susceptible to ultra-violet radiation, e.g. benzoin, benzoin ethers, alpha,alpha-dimethoxy-alpha-phenylacetophenone, diethoxyacetophenone, alpha-hydroxy-alpha,alpha-dimethylactophenone, and 1-benzoylcyclohexanol.

The amount of radiation necessary to cure the composition will of course depend on the angle of exposure to the radiation, the thickness of the coating to be applied, and the amount of polymerizable groups in the coating composition, as well as the presence or absence of a free radical initiating catalyst. For any given composition, experimentation to determine the amount of radiation sensitive pi bonds not cured following exposure to the radiation source is the best method of determining the amount and duration of the radiation required. Typically, an ultra-violet source with a wavelength between 200 and 300 nm (e.g. a filtered mercury arc lamp) is directed at coated surfaces carried on a conveyor system which provides a rate of passage past the ultra-violet source appropriate for the radiation absorption profile of the composition (which profile is influenced by the degree of cure desired, the thickness of the coating to be cured, and the rate of polymerization of the composition).

The polymerizable compositions of this invention may also find use as a starting material for applications in addition to coatings. Particular examples include articles formed by the shaping (e.g. casting, molding, or extrusion) of polymeric materials, as well as binders (e.g. for pigments of printing inks, magnetic media, etc.), or by use of the composition as an adhesive or sealant. Further, steric polymerization techniques as described by E. J. Murphy et al., "Some Characteristics of Steric Polymerization", *Proceedings of RadTech 1990-North America*, vol. I, pp. 217–226, the disclosure of which is incorporated herein by reference, may be useful. In such techniques, where a pool of polymerizable composition is subjected to a focused laser beam of ultra-violet radiation, an object is formed within the pool from discrete thin layers formed at the top of the pool where the laser beam is focused. In a sense, the composition polymerizes in contact with the surface of a layer of cured polymer. The particular procedures used and the choice of the other necessary or desirable starting materials, catalysts, and other functional additives, as well as the amount of N,N'-acylamido-piperazine compound, will be within the skill of the art within which the crosslinked polymeric composition is employed.

U.S. Ser. No. 08/242,797, filed May 19, 1994, which is a continuation-in-part of U.S. Ser. No. 08/073,014, filed Jun. 4, 1993, the disclosures of which are incorporated herein by reference, discloses acrylamido-piperazine compounds useful in radiation curable coatings.

The following examples will serve to further illustrate the invention, but should not be construed to limit the invention, unless expressly set forth in the appended claims. All parts, percentages, and ratios are by weight unless otherwise indicated in context.

EXAMPLES

Coating Procedures and Apparatus

In the following examples, coatings were prepared by the following procedure. The substrates used, unless noted otherwise, were aluminum panels available commercially as Q-panels from Q-Panel Corporation, and are coated using RDS Coating Rods. The curing apparatus was a Fusions Systems Model F440 with a 300 watt/inch mercury bulb. The variables in the tests include the speed of the belt which transports the substrate under the bulb, the number of passes the substrate makes under the bulb, and the thickness of the coating on the substrate, and variations in the coating formulation, e.g. type and amount of additives and co-monomers, which will be noted below.

EXAMPLE 1

Preparation of the bis-Piperazine Acrylamide Derivative of Benzophenone Tetracarboxylic Dianhydride 16.1 grams (50 mmol) benzophenone 3,4,3',4'-tetracarboxylic acid dianhydride and 0.31 grams (2.5 mmol) dimethylaminopyridine were charged into a 250 ml three-necked round-bottom flask. 150 ml of acetonitrile was added to this mixture, forming a slurry of partially dissolved anhydride. A slurry of 8.6 grams piperazine in a mixture of 60 ml acetonitrile and 20 ml dichloromethane was added in one portion to the stirred anhydride slurry. The temperature of the reaction mixture increased, and a milky white precipitate was formed. After extended mixing, the principal portion of the solvent was removed by rotary evaporation to yield 32.4 grams of a light tan, powdery solid.

The reaction product was charged into a 500 ml 3-necked round-bottomed flask equipped with magnetic stirring, an addition funnel, and nitrogen. To this mixture was added 7.2 grams acrylic acid (100 mmol) and 200 ml pyridine. 22.7 grams (110 mmol) dicyclohexylcarbodiimide and 1.22 grams (10 mmol) dimethylaminopyridine were dissolved in 50 ml dichloromethane and charged into the addition funnel. The solution was added over a period of two hours, and the reaction mixture was allowed to stir overnight. Infrared analysis showed almost complete disappearance of the dicyclohexylcarbodiimide.

The solid was filtered and collected in a Buchner funnel, and the resulting red solution was stripped of solvent in a rotary evaporator, mixed with an additional 50 ml dichloromethane to precipitate additional urea. The mixture was filtered, and solvent removal by rotary evaporation yielded 9 grams of a tarry red solid. Analysis by Thin Layer Chromatography (4% Methanol/Chloroform) shows several components, some major ones with large $R_f$, none of which corresponds to starting material. Aside from possible oligomeric materials, there are three possible isomeric products, so the number of high $R_f$ materials is not unexpected.

A 0.0254 mm (1 mil) film of the material, cast as a 60% solution in deuterochloroform, cured in one pass at 100 feet/minute, yielding a film with 100% adhesion on aluminum, BH pencil hardness, and 1 MEK rub. A 2.5 mil film of the same material cured in 4 passes at 100 feet/minute, yielding a film with BH pencil hardness, 100% adhesion, and 5 MEK rubs. These tests were carried out with no added photoinitiator, as the materials are self-curing.

EXAMPLE 2

Preparation of the bis-Piperazine Acrylamide Derivative of Pyromellitic Dianhydride (Benzentetracarboxylic Dianhydride)

Into a 250 ml round-bottomed three-necked flask were charged 8.6 grams (100 mmol) piperazine, 0.12 grams (1 mmol) dimethylaminopyridine, 100 ml acetonitrile, 50 ml dichloromethane, and 10 ml acetone. A slurry of 10.9 grams (50 mmol) pyromellitic acid dianhydride (i.e. the dianhydride of benzene-1,2,4,5-tetracarboxylic acid), 50 ml acetonitrile, and 20 ml acetone was added through an addition funnel to the reaction flask, leading to immediate formation of a white suspension accompanied by a rise in temperature. The reaction mixture was allowed to stir for an extended period, and filtered to yield 21.9 grams of a light orange powder.

The reaction product, together with 7.2 grams (100 mmol) acrylic acid, 1.22 grams (10 mmol) dimethylaminopyridine, and 150 ml pyridine were charged into a 500 ml three-necked flask equipped with a magnetic stirrer. 20.6 grams (100 mmol) dicyclohexylcarbodiimide were dissolved in 50 ml dichloromethane and added to the stirred mixture. After stirring overnight, most of the pyridine was removed on a rotary evaporator, 100 ml dichloromethane were added to the resulting semisolid, and the undissolved urea was filtered from the solution. The solvent was removed by rotary evaporation to yield 9.9 grams of a slightly yellow viscous liquid.

What is claimed is:

1. A compound of the formula:

$$\left[\begin{array}{c}R^1\\ \\R^2\end{array}\!\!\!\!\!\!\begin{array}{c}O\\ \|\\ \\R^3\end{array}\!\!\!-N\!\!\bigcirc\!\!N\!\!-\!\!(B^1)_x\right]_a \left[(B^2)_m\!\!-N\!\!\bigcirc\!\!N\!\!-\!\!\begin{array}{c}O\\ \|\\ \\R^3\end{array}\!\!\!\!\begin{array}{c}R^1\\ \\R^2\end{array}\right]_b$$

$$R^{23}$$

$$\left[\begin{array}{c}R^1\\ \\R^2\end{array}\!\!\!\!\!\!\begin{array}{c}O\\ \|\\ \\R^3\end{array}\!\!\!-N\!\!\bigcirc\!\!N\!\!-\!\!(B^4)_n\right]_d \left[(B^3)_y\!\!-N\!\!\bigcirc\!\!N\!\!-\!\!\begin{array}{c}O\\ \|\\ \\R^3\end{array}\!\!\!\!\begin{array}{c}R^1\\ \\R^2\end{array}\right]_c$$

wherein:

$R^1$, $R^2$, and $R^3$ are each independently selected from the group consisting of hydrogen and methyl;

$B^1$, $B^2$, $B^3$, and $B^4$ are linking groups independently selected from the group consisting of carbonyl, sulfonyl, amide, and carboxyl;

a, b, c, and d are independently one or zero provided that the sum of a, b, c and d is at least three: m, n, x, and y are independently one or zero;

$R^{23}$ is a group selected from the group consisting of phenyl, phenyl substituted with at least one member selected from the group consisting of alkyl, alkenyl, alkoxy, halogen, nitro, sulfonic acid, $C_{1-10}$ alkyl sulfonate ester, carboxyl, and trihalomethyl, benzophenonyl, and benzophenonyl substituted with at least one member selected from the group consisting of alkyl, alkenyl, alkoxy, halogen, nitrogen, nitro, sulfonic acid, $C_{1-10}$ alkyl sulfonate ester, carboxyl and trihalomethyl.

2. A compound of claim 1 wherein said $R^{23}$ group is phenyl.

3. A compound of claim 1 wherein said $R^{23}$ group is benzophenonyl.

4. A compound of claim 1 wherein each $B^1$, $B^2$, $B^3$, and $B^4$ is a carbonyl group.

5. A compound of claim 1 wherein each $B^1$, $B^2$, $B^3$, and $B^4$ is a sulfonyl group.

6. A compound of claim 1 wherein each $B^1$, $B^2$, $B^3$, and $B^4$ is an amide group.

7. A compound of claim 1 wherein each $B^1$, $B^2$, $B^3$, and $B^4$ is a carboxyl group.

8. A compound of claim 1 wherein $R^{23}$ has substituents selected from the group consisting of carboxyl and carboxylate salt substituents.

9. A compound of claim 1 wherein $R^1$ and $R^2$ are hydrogen and $R^3$ is hydrogen or methyl.

10. A compound of claim 1 wherein $R^1$, $R^2$, and $R^3$ are hydrogen.

11. A compound having the formula:

$$\left[M\!-\!O\!-\!\!\begin{array}{c}O\\ \|\\ C\end{array}\right]_s\!\!-\!\!R^{23}\!\!-\!\!\left[\begin{array}{c}O\\ \|\\ C\end{array}\!\!-N\!\!\bigcirc\!\!N\!\!-\!\!\begin{array}{c}O\\ \| \\ \end{array}\!\!\!\!\begin{array}{c}R^1\\ \\R^2\end{array}\right]_t$$

wherein each $R^1$, $R^2$, and $R^3$ is independently selected from the group consisting of hydrogen and methyl;

$R^{23}$ is a group selected from the group consisting of phenyl, phenyl substituted with at least one member selected from the group consisting of alkyl, alkenyl, alkoxy, halogen, nitro, sulfonic acid, $C_{1-10}$ alkyl sulfonate ester, carboxyl and trihalomethyl, benzophenonyl, and benzophenonyl substituted with at least one member selected from the group consisting of alkyl, alkenyl, alkoxy, halogen, nitro, sulfonic acid, $C_{1-10}$ alkyl sulfonate ester, carboxyl and trihalomethyl;

s and t are integers, provided that s and t are least one each; and

M is hydrogen or a counter-ion of a salt of said compound.

12. A compound of claim 11 wherein $R^{23}$ is a phenyl group that is otherwise unsubstituted.

13. A compound of claim 11 wherein $R^{23}$ is a benzophenonyl group that is otherwise unsubstituted.

14. A compound of claim 11 wherein M is hydrogen.

15. A compound of claim 11 wherein each of s and t is two.

16. A compound of claim 11 wherein $R^1$ and $R^2$ are hydrogen and $R^3$ is hydrogen or methyl.

17. A compound of claim 11 wherein $R^1$, $R^2$, and $R^3$ are hydrogen.

* * * * *